United States Patent [19]

Lin

[11] Patent Number: 5,722,831

[45] Date of Patent: Mar. 3, 1998

[54] APPARATUS FOR FASTENING A MATRIX BAND TO A TOOTH

[76] Inventor: Chih-Sheng Lin, No. 184, Ching-Yun Rd., Tu-Chen City, Taipei Hsien, Taiwan

[21] Appl. No.: 770,558

[22] Filed: Dec. 20, 1996

[51] Int. Cl.$^6$ .................................................. A61C 5/04
[52] U.S. Cl. ................................................................ 433/155
[58] Field of Search .................................................. 433/155

[56] References Cited

U.S. PATENT DOCUMENTS

| | | | |
|---|---|---|---|
| 2,286,021 | 6/1942 | Stanford | 433/155 |
| 3,425,125 | 2/1969 | Bergendal | 433/155 |
| 3,436,831 | 4/1969 | Tofflemire | 433/155 |
| 5,460,525 | 10/1995 | Rashid | 433/155 |

*Primary Examiner*—John J. Wilson
*Attorney, Agent, or Firm*—Christensen O'Connor Johnson & Kindness PLLC

[57] ABSTRACT

An apparatus for fastening a matrix band to a tooth includes an elongated frame, an elongated slide member, a locking unit and a single-direction positioning mechanism. A front end of the support frame is formed with a retaining member which engages slidably overlapping end portions of the matrix band in order to orient selectively a loop portion of the matrix band to predetermined directions. The slide member engages slidably and parallelly with the support frame. A front end of the slide member is formed with a sliding block. The locking unit is provided on the sliding block of the slide member for locking releasably the overlapping end portions in the sliding block. The single-direction positioning mechanism permits the sliding block of the slide member to move away from the retaining member in order to pull the overlapping end portions of the matrix band to move rearward, but locks releasably the slide member relative to the support frame in order to prevent the sliding block from being moved toward the retaining member.

7 Claims, 7 Drawing Sheets

APPARATUS FOR FASTENING A MATRIX BAND TO A TOOTH

BACKGROUND OF THE INVENTION

1. Field of the Invention

This invention relates to an apparatus for fastening a matrix band to a tooth in operative dentistry.

2. Description of the Related Art

Referring to FIG. 1, a conventional apparatus 1 for fastening a matrix band 2 to a tooth is shown to comprise an elongated support frame 11, a sliding block 12, a threaded rod 13 and a nut member 14. The matrix band 2 is in the form of an elongated thin strip and has two ends 21 which are to be overlapped in order to form a loop portion 22 to be sleeved onto a carious tooth. The support frame 11 has a U-shaped retaining member 111 with two slits 112 at a front end of the support frame 11 in order to orient selectively the loop portion 22 of the matrix band 2 to predetermined directions. The support frame 11 further has a U-shaped engaging portion 113 formed at a rear end thereof. The sliding block 12 engages slidably the support frame 11 and has an inclined slit 121 and a threaded hole 122 extending through the inclined slit 121. The nut member 14 has an annular groove 141 formed at one end thereof. The annular groove 141 engages rotatably the U-shaped engaging portion 113 of the support frame 11. The threaded rod 13 engages threadedly the nut member 14 and the threaded hole 122 of the sliding block 12 and extends through the U-shaped engaging portion 113 of the support frame 11. Therefore, the overlapping end portions of the matrix band 2 can be inserted into the inclined slit 121 and the threaded hole 122 so as to be clamped by a front end of the threaded rod 13. The connection of the loop portion 22 and the overlapping end portions of the matrix band 2 is retained by the U-shaped retaining member 111.

In use, the loop portion 22 of the matrix band 2 is sleeved onto a carious tooth, and the threaded rod 13 is rotated manually in order to permit the sliding block 12 to move away from the retaining member 111, thereby increasing the length of the overlapping end portions and reducing the size of the loop portion 22 of the matrix band 2. Thus, the carious tooth is sleeved tightly by the loop portion 22 of the matrix band 2. The loop portion 22 of the matrix band 2 may be released from the carious tooth by means of rotating reversely the nut member 14.

However, the conventional fastening apparatus suffers from slow movement of the sliding block 12 relative to the retaining member 111 by means of rotating the nut member 14. In addition, the conventional fastening apparatus will wobble during the rotation of the nut member 14, thus resulting in wobbling of the matrix band 2 which may hurt the patient's gingiva or mucosa.

SUMMARY OF THE INVENTION

It is therefore a main object of the present invention to provide an apparatus for fastening a matrix band to a tooth in which the matrix band can be quickly and stably fastened to and releasably from a carious tooth.

According to one aspect of the present invention, an apparatus for fastening a matrix band to a tooth comprises:

- an elongated support frame having front and rear ends, the front end of the support frame being formed with a retaining member which engages slidably overlapping end portions of the matrix band in order to orient selectively a loop portion of the matrix band to predetermined directions;

- an elongated slide member engaging slidably and parallelly the support frame and having front and rear ends, the front end of the slide member being formed with a sliding block;

- locking means provided on the sliding block of the slide member for locking releasably the overlapping end portions in the sliding block; and

- a single-direction positioning mechanism for permitting the sliding block of the slide member to move away from the retaining member of the support frame in order to pull the overlapping end portions of the matrix band to move rearward, thereby reducing the size of the loop portion of the matrix band, but locking releasably the slide member relative to the support frame in order to prevent the sliding block from being moved toward the retaining member.

According to another aspect of the present invention, an apparatus is adapted to fasten two matrix bands to two teeth. Each of the matrix bands has length-variable overlapping end portions and a loop portion extending from the overlapping end portions. The apparatus comprises:

- an elongated support frame having front and rear ends and two opposite faces, the support frame having two retaining members which are formed spacedly adjacent to the front end of the support frame, each of the retaining members engaging slidably the overlapping end portions in order to orient selectively the loop portion of the matrix band to predetermined directions;

- two elongated slide members, each of the slide members engaging slidably and parallelly a respective one of the opposite faces of the support frame and having front and rear ends, the front end of each of the slide members being formed with a sliding block;

- two locking means, each being provided on the sliding block of a respective one of the slide members for locking releasably a corresponding of the overlapping end portions in the sliding block of the respective one of the slide members; and

- two single-direction positioning mechanisms, each permitting the sliding block of the respective one of the slide members to move away from a corresponding one of the retaining members of the support frame, but locking releasably the respective one of the slide members relative to the support frame in order to prevent the sliding block of the respective one of the slide members from being moved toward the corresponding one of the retaining members.

BRIEF DESCRIPTION OF THE DRAWINGS

Other features and advantages of this invention will become apparent in the following detailed description of the preferred embodiments of this invention with reference to the accompanying drawings, in which.

DETAILED DESCRIPTION OF THE PREFERRED EMBODIMENTS

Figure 1:
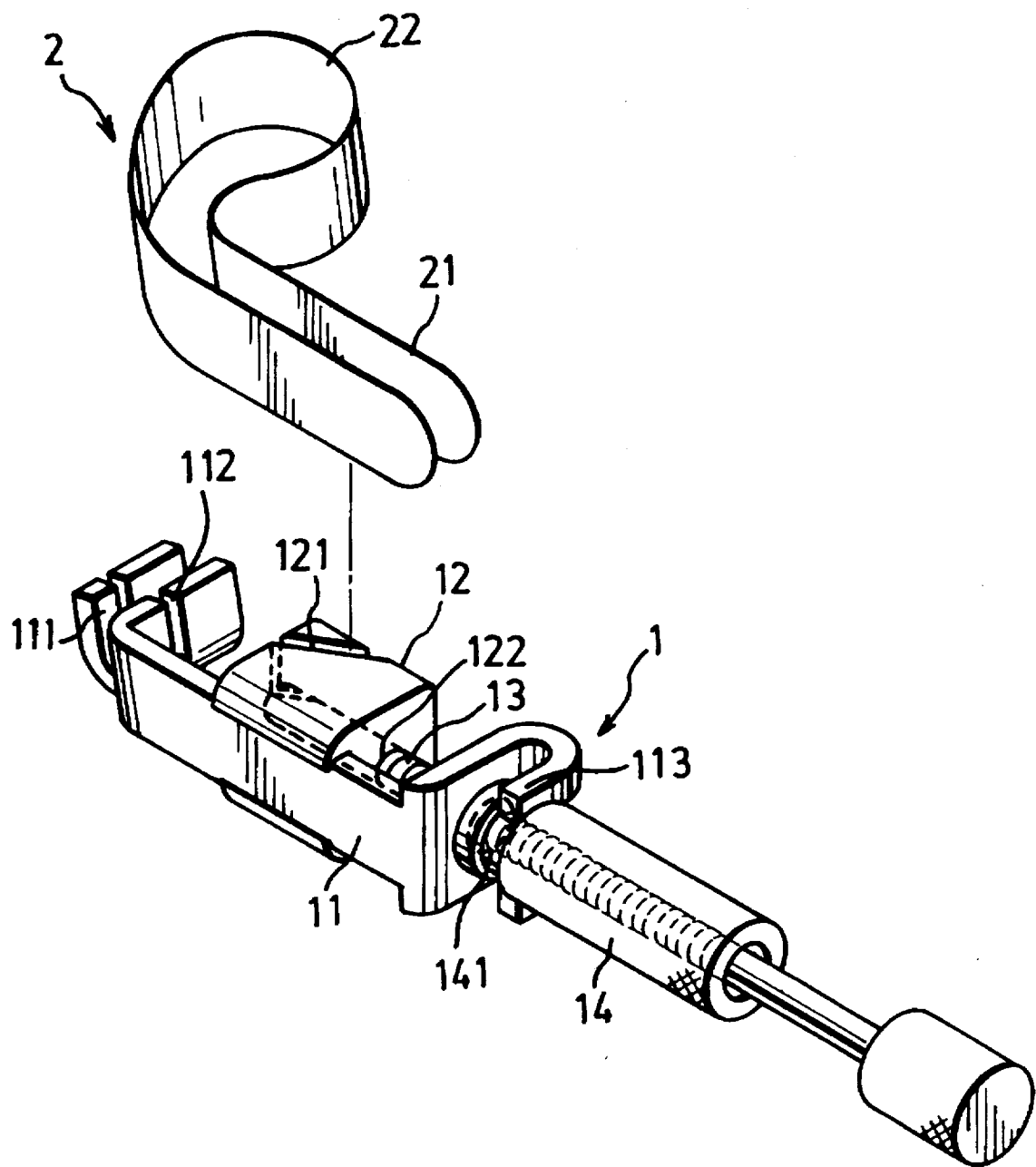
FIG. 1 is a perspective view of a conventional apparatus for fastening a matrix band to a tooth.

Before the present invention is disclosed in greater detail, it should be noted that like elements are denoted by the same reference numerals throughout the disclosure.

Figure 2:
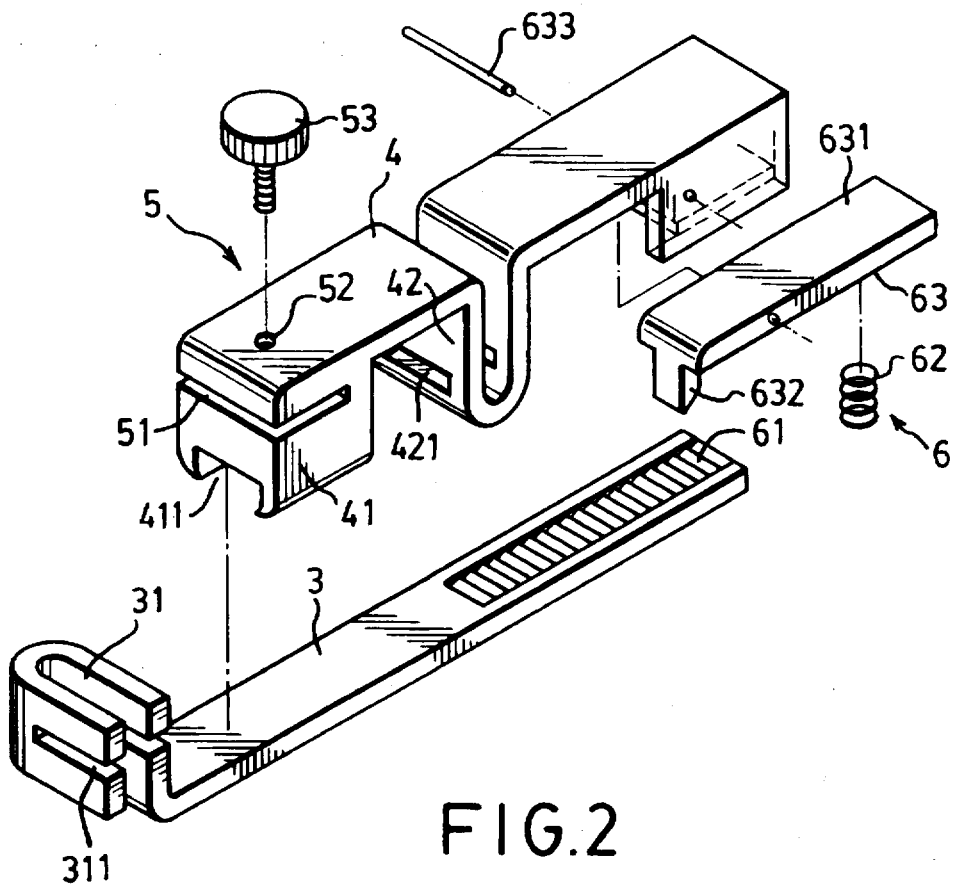
FIG. 2 is an exploded perspective view of a first preferred embodiment of an apparatus for fastening a matrix band to a tooth according to the present invention.
Figure 3:
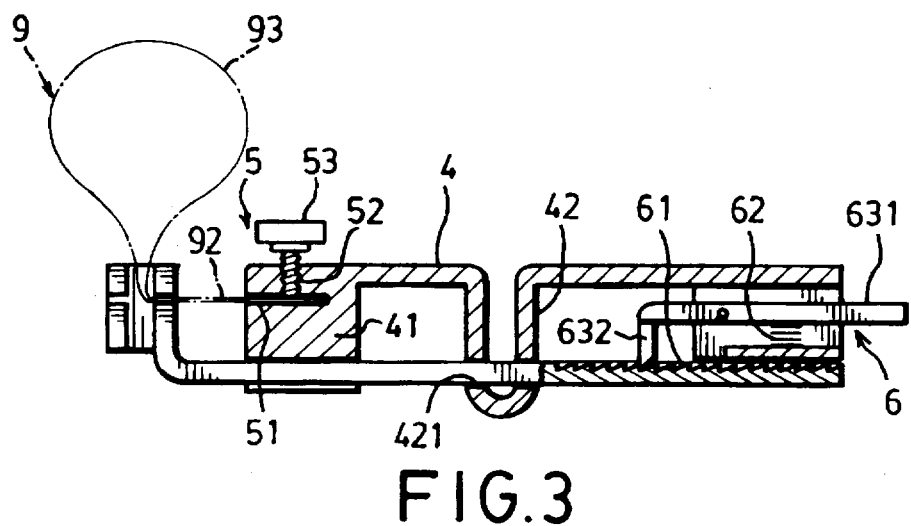
FIG. 3 is a sectional schematic view of the first preferred embodiment of the fastening apparatus of the present invention.

Referring to FIGS. 2 and 3, a first preferred embodiment of an apparatus for fastening a matrix band 9 is shown to comprise an elongated support frame 3, an elongated slide member 4, locking means 5 and a single-direction positioning mechanism 6.

The front end of the support frame 3 is formed with a U-shaped retaining member 31 having two positioning slits formed therein. The retaining member 31 engages slidably overlapping end portions 92 of the matrix band 9 in order to orient selectively a loop portion 93 of the matrix band 9 to predetermined directions. In this embodiment, the loop portion 93 is bent to a perpendicular direction relative to the support frame 3.

The slide member 4 engages slidably and parallelly the support frame 3. The slide member 4 has a sliding block 41 formed at a front end thereof and a U-shaped support 42 formed at an intermediate portion thereof. The sliding block 41 has an engaging groove 411 which engages slidably the support frame 3. The U-shaped support 42 has a through hole through which the support frame 3 passes.

The locking means 5 is provided on the sliding block 41 of the slide member 4 for locking releasably the overlapping end portions 92 in the sliding block 41. The locking means 5 includes a slit 51 which is formed in a front end of the sliding block 41 in order to receive the overlapping end portions 92 of the matrix band 9, a threaded hole 52 which is formed in the sliding block 41 and which is communicated transversely with the slit 51, and a locking bolt 53 threaded into the threaded hole 52 in order to fasten the overlapping end portions 92 in the slit 51 of the sliding block 41, as best illustrated in FIG. 3.

The single-direction positioning mechanism 6 includes an L-shaped catch member 63 and a plurality of detent teeth 61 formed adjacent to the rear end of the support frame 3. The L-shaped catch member 63 has a horizontal arm 631 which is connected pivotally adjacent to the rear end of the slide member 4 between the slide member 4 and the support frame 3 by means of a pin 633. A detent pawl 632 extends downwardly from a front end of the horizontal arm 631. A spring member 62 is connected to the rear end of the slide member 4 in order to bias the horizontal arm 631 to rotate and cause the detent pawl 632 to engage one of the detent teeth 61. Therefore, the sliding block 41 can be moved away from the retaining member 31 while the detent pawl 632 slides over the detent teeth 61, and is prevented from being moved toward the retaining member 31 when the sliding block 41 is moved away from the retaining member 31 due to the engagement of the detent pawl 632 and one of the detent teeth 61. The size of the loop portion 93 of the matrix band 9 is decreased gradually when the user grasps the U-shaped support 42 of the slide member 4 with his fingers in order to move the sliding block 41 away from the retaining member 31 so that the loop portion 93 is sleeved firmly on a carious tooth (not shown). By depressing a rear end of the horizontal arm 631, the detent pawl 631 disengages one of the teeth 61 so that the user can push the slide member 4 forward to allow the sliding block 41 to move toward the retaining member 31 in order to release the matrix band 9 from the carious teeth.

It is noted that the slide member 4 can be moved quickly and stably with respect to the support frame 3 in order to permit the matrix band 9 to be tied onto or released from the carious teeth.

Figure 4:
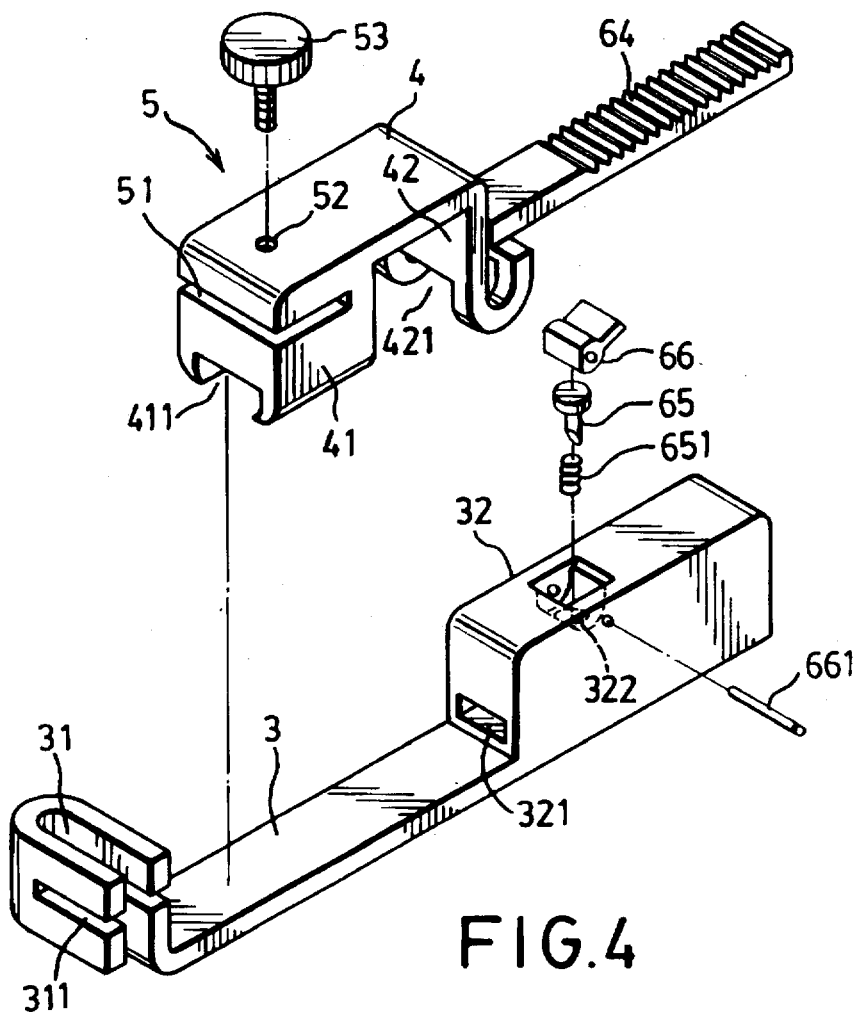
FIG. 4 is an exploded perspective view of a second preferred embodiment of an apparatus for fastening a matrix band to a tooth according to the present invention.
Figure 5:
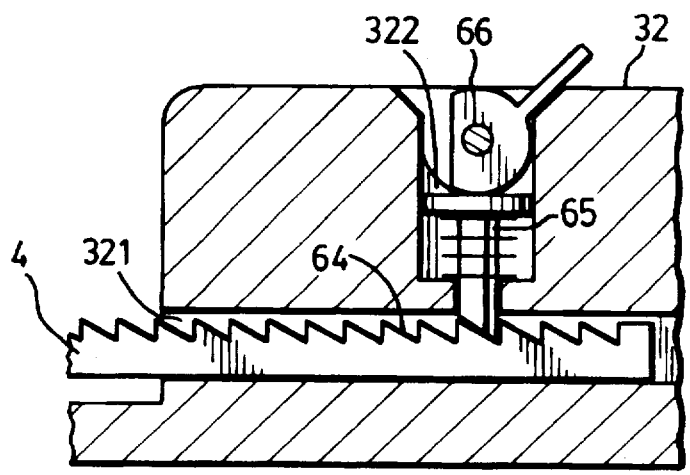
FIG. 5 is a fragmentary sectional view illustrating a single-direction positioning mechanism of the second preferred embodiment of the fastening apparatus of the present invention.

Referring to FIG. 4, a second preferred embodiment of an apparatus for fastening a matrix band to a tooth of the present invention is shown. In this embodiment, the structures of the support frame 3, the slide member 4 and the locking means 5 are similar to those of the first embodiment. However, the single-direction positioning mechanism of the second preferred embodiment comprises a plurality of detent teeth 64 which are formed adjacent to the rear end of the slide member 4, and an elongated housing 32 which is formed longitudinally adjacent to the rear end of the support frame 3. The housing 32 has a longitudinal hole 321 for receiving the rear end of the slide member 4 on which the detent teeth 64 are formed. A transverse hole 322 extends from a top face of the housing 32 to the longitudinal hole 321 in the housing 32. A lock pin 65 is received in the transverse hole 322, and a coiled spring 651 is mounted in the transverse hole 322 in order to bias the lock pin 65 to move toward the top face of the housing 32. A cam member 66 is connected pivotably to the housing 32 within the transverse hole 322 by means of a pivot pin 661. The cam member 66 is rotatable to a first position where the lock pin 65 is pushed by the cam member 66 against the biasing force of the coiled spring 651 so as to engage one of the detent teeth 64 of the support frame 4, as best illustrated in FIG. 5. Therefore, the sliding block 41 can be moved away from the retaining member 31 member but is prevented from being moved toward the retaining member 31 when the sliding block 41 is moved away from the retaining member 31. The cam member 66 is further rotatable to a second position wherein the lock pin 65 is biased by the coiled spring 651 so as to disengage one of the detent teeth 64. Therefore, the sliding block 41 of the slide member 4 can be moved freely toward the retaining member 31 of the support frame 3 in order to release the loop portion 93 of the matrix band 9.

Figure 6:
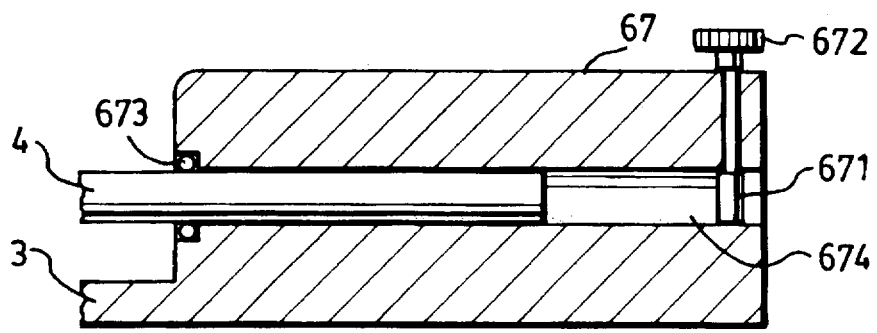
FIG. 6 is a fragmentary sectional view illustrating another preferred embodiment of a single-direction positioning mechanism of the fastening apparatus according to the present invention.

FIG. 6 shows a modification of the single-direction positioning mechanism 6 of the second preferred embodiment. The single-direction positioning mechanism comprises an elongated housing 67 formed adjacent to the rear end of the support frame 3. The housing 67 has a longitudinal through hole 674 with a front end through which the rear end of the slide member 4 extends. A seal member 673 is mounted adjacent to the front end of the longitudinal through hole 674 and contacts the slide member 4 so that the slide member 4 is extendible slidably and sealingly into the longitudinal through hole 674. A check valve member 671 is mounted adjacent to the rear end of the housing 67, thereby permitting air to flow from the longitudinal hole 674 to the exterior of the housing 67 but preventing air from flowing into the longitudinal through hole 674 via the check valve member 671. Therefore, the sliding block 41 can move away from the retaining member 31 while the air is forced out of the rear end of the housing 67 via the check valve member 671 by means of the rear end of the slide member 4, but is prevented from being moved toward retaining member 31 when the sliding block 41 is moved away from the retaining member 31 due to the negative pressure in the housing 67. The slide member 4 can be released to move freely in the housing 67 by opening the check valve member 671 and allowing air to flow into the longitudinal through hole 674 by rotating the rotary shaft 672.

Figure 7:
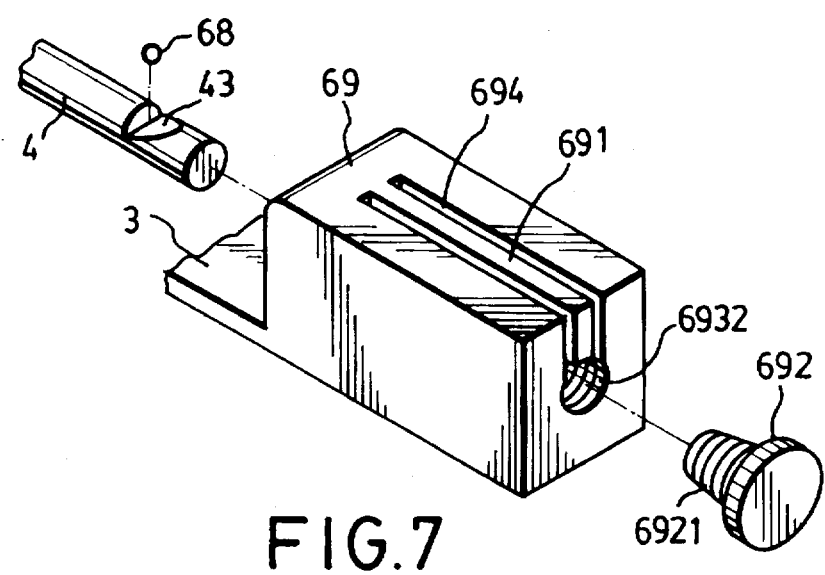
FIG. 7 is a fragmentary exploded view of still another preferred embodiment of a single-direction positioning mechanism of the fastening apparatus according to the present invention.
Figure 8:
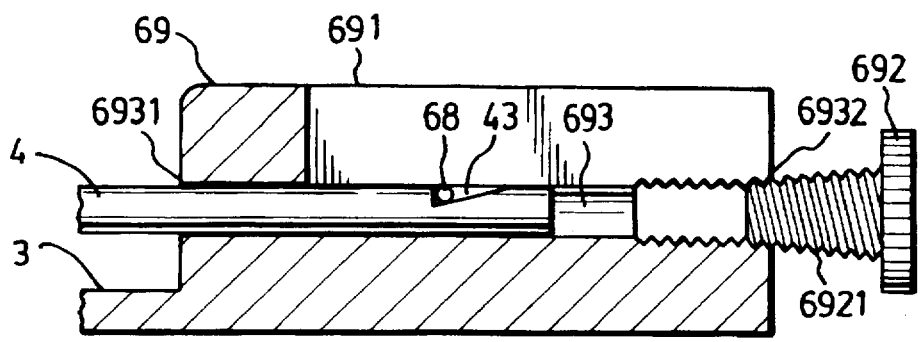
FIG. 8 is a fragmentary sectional view of the single-direction positioning mechanism of FIG. 7.

Referring to FIGS. 7 and 8, another preferred embodiment of a single-direction positioning mechanism is shown to comprise a wedge-shaped groove 43 formed transversely in an external face of the slide member 4 adjacent to the rear end of the slide member 4, a steel ball 68 disposed in the wedge-shaped groove 43, and an elongated housing 69 formed adjacent to the rear end of the support frame 3. The housing 69 has a longitudinal through hole 693 with a front end 6931 through which the rear end of the slide member 4 extends and a threaded rear end 6932. Two slits 694 extend from the threaded rear end 6932 and are communicated with the longitudinal through hole 693 in order to form a resilient tongue 691 adjacent to the threaded rear end 6932 of the housing 69. A screw member 692 with a tapered, externally threaded shaft 6921 engages threadedly the threaded rear end 6932 of the longitudinal through hole 693. The ball 68 is rolled and clamped between the slide member 4 and an internal wall face of the longitudinal through hole 693 in order to prevent the sliding block 41 from being moved toward the retaining member 31. The ball 68 is released when the screw member 692 is threaded into the threaded rear end 6932 in order to lift the resilient tongue 691, thereby permitting free movement of the slide member 41 relative to the support frame 3.

Figure 9:
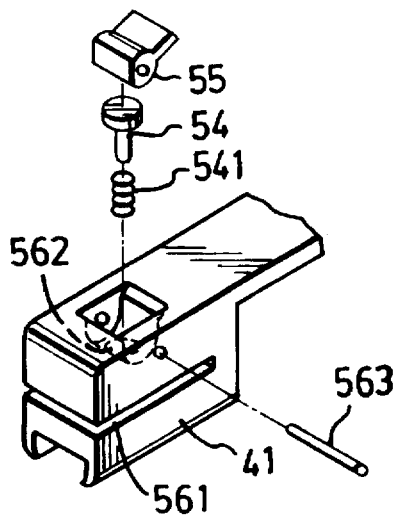
FIG. 9 is a fragmentary exploded view of another preferred embodiment of a locking means which is mounted to a sliding block of the fastening apparatus according to the present invention.
Figure 10:
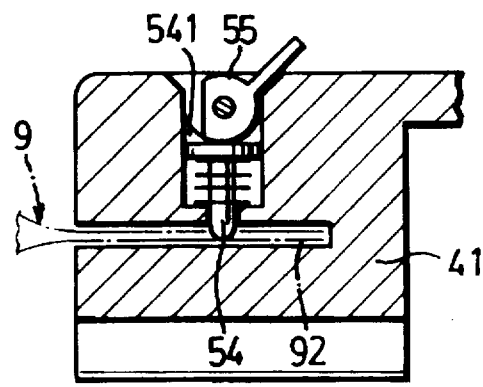
FIG. 10 is a sectional view of the locking means of FIG. 9.

FIGS. 9 and 10 show another preferred embodiment of a locking means 5 of the fastening apparatus according to the present invention. In this embodiment, the locking means 5 comprises a slit 561 which is formed in a front end of the sliding block 41 in order to receive the overlapping end portions 92 of the matrix band 9. A transverse hole 562 extends from an external face of the sliding block 41 to the slit 561. A lock pin 54 is received in the transverse hole 562, and a coiled spring 541 is mounted in the transverse hole 562 in order to bias the lock pin 54 to move toward the external face of the sliding block 41. A cam member 55 is connected pivotably to the sliding block 41 within the transverse hole 562 by means of a pivot pin 563. The cam member 55 is rotatable to a first position where the lock pin 54 is pushed by the cam member 55 against the biasing force of the coiled spring 541 so as to engage the overlapping end portions 92 of the matrix band 9, thereby preventing separation of the overlapping end portions 92 from the sliding block 41, as best illustrated in FIG. 10, and a second position wherein the lock pin 54 is biased by the coiled spring 541 so as to disengage from the overlapping end portions 92 of the matrix band 9.

Figure 11:
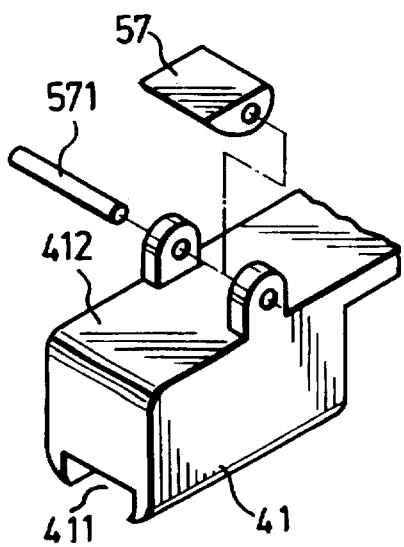
FIG. 11 is a fragmentary exploded view of still another preferred embodiment of a locking means which is mounted to a sliding block of the fastening apparatus according to the present invention.
Figure 12:
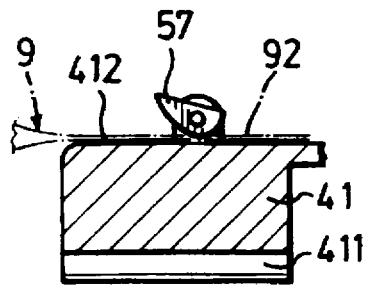
FIG. 12 is a sectional view of the locking means of FIG. 11.

FIGS. 11 and 12 show still another preferred embodiment of a locking means of the fastening apparatus according to the present invention. In this embodiment, the locking means comprises a cam member 57 mounted rotatably to the sliding block 41 by means of a pivot pin 571 so that the overlapping end portions 92 of the matrix band 9 can be clamped between the cam member 57 and an external face 412 of the sliding block 41 when the cam member 57 is rotated to a first position, and can be disengaged from the cam member 57 and the sliding block 41 when the cam member 57 is rotated to a second position, as best illustrated in FIG. 12.

Figure 13:
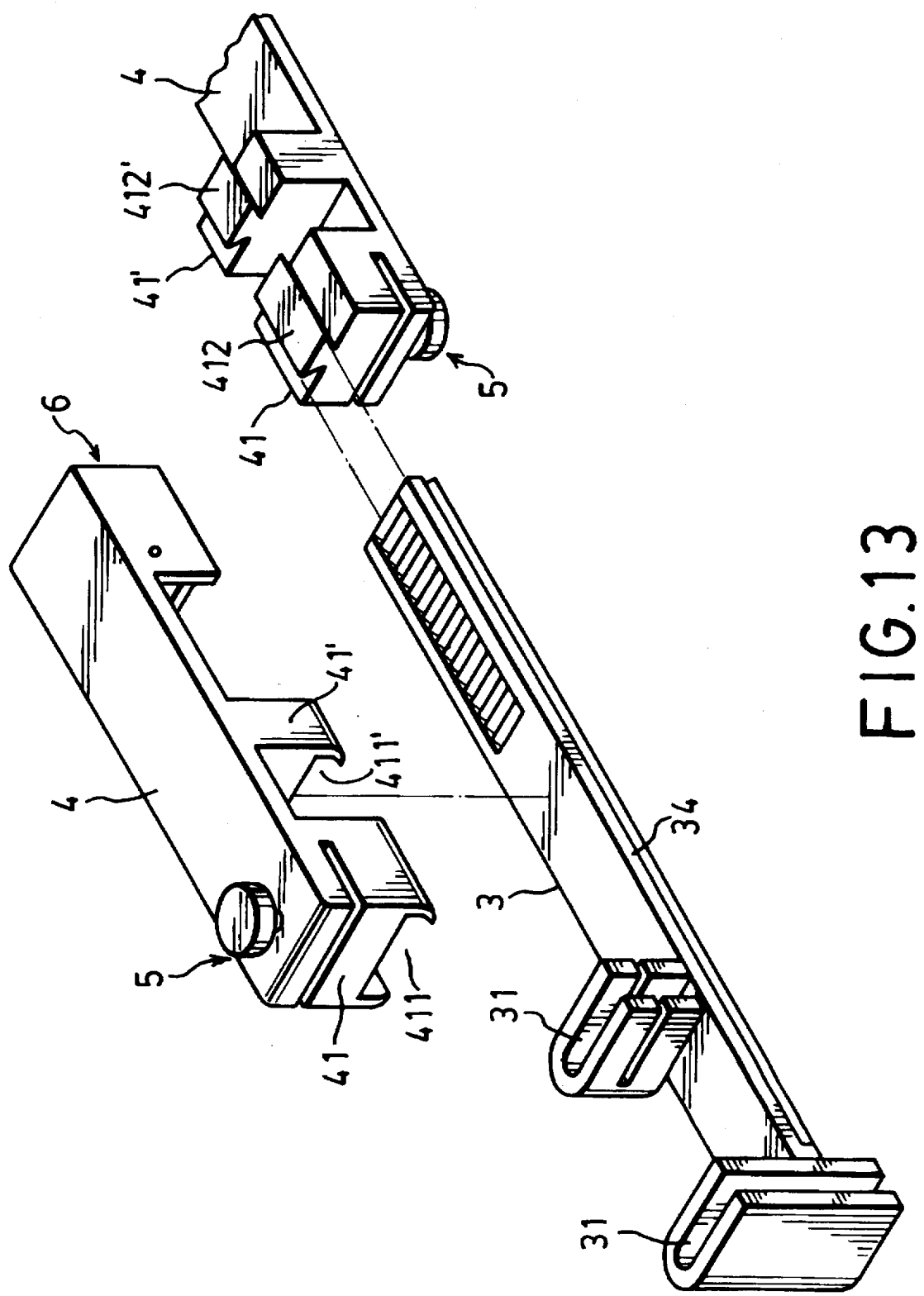
FIG. 13 is a fragmentary exploded view of a third preferred embodiment of a fastening apparatus according to the present invention.
Figure 14:
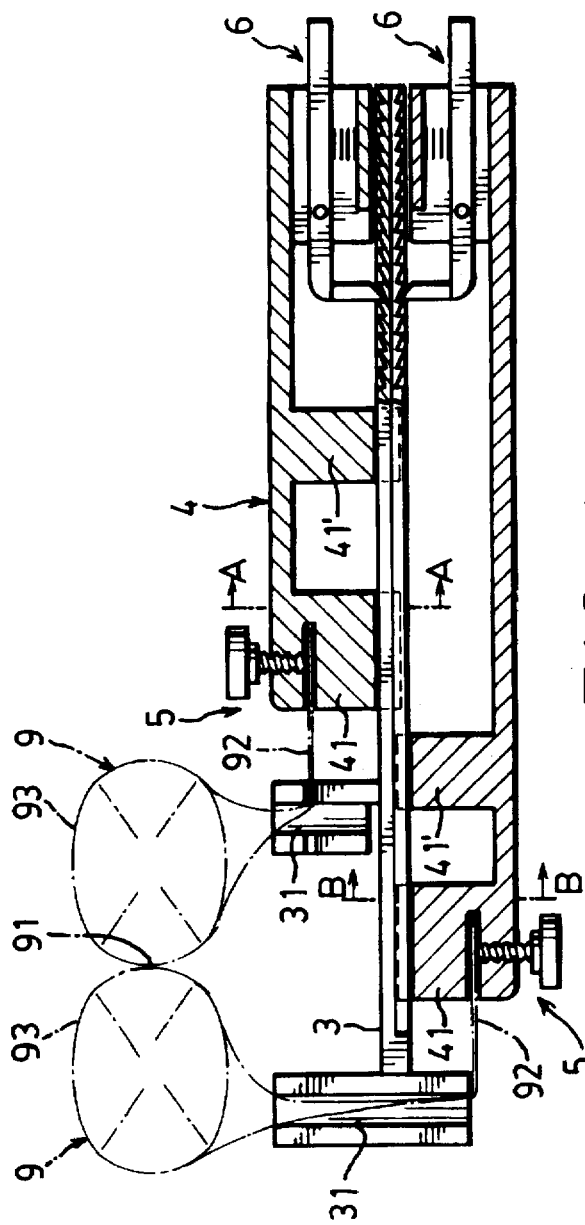
FIG. 14 is a sectional view of the third preferred embodiment of FIG. 13.

Referring to FIGS. 13 and 14, a third preferred embodiment of a fastening apparatus is used to fasten two matrix bands to two teeth. Each of the matrix bands 9 has length-variable overlapping end portions 92 and a loop portion 93 extending from the overlapping end portions 92. The two loop portions 93 are spot-welded to each other at a point 91 which is to be disposed on a contact area of two adjacent teeth. The fastening apparatus comprises an elongated support frame 3, two elongated slide members 4, two locking means 5 and two single-direction positioning mechanisms 6.

Figure 16:
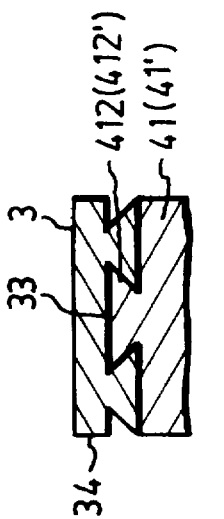
FIG. 16 is a cross sectional view taken along the lines B—B of FIG. 13.
Figure 15:
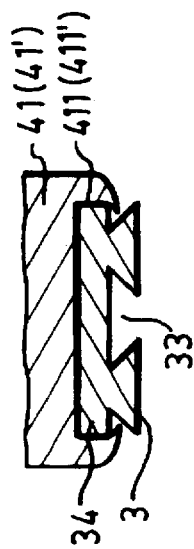
FIG. 15 is a cross sectional view taken along the lines A—A of FIG. 13.

The support frame 3 has two retaining members 31 which are formed spacedly adjacent to a front end thereof. The structure and action of the retaining members 31 are the same as those of the first embodiment. Each of the slide members 4 engaging slidably and parallelly a respective one of the opposite faces of the support frame 3. The front end of each of the slide members 4 is formed with two spaced sliding blocks 41, 41'. The lower faces of the sliding blocks 41, 41' of the upper slide member 4 are formed with sliding grooves 411, 411' which engage slidably two opposite rails 34 formed on the upper portion of the support frame 3, as best illustrated in FIG. 15. The upper faces of the sliding blocks 41, 41' of the lower slide member 4 are formed with dovetail projections 412, 412' which engage slidably a dovetail groove 33 formed in the lower face of the support frame 3, as best illustrated in FIG. 16. Each of the locking means 5 is provided on the sliding block 41 of a respective one of the slide members 4 for locking releasably the overlapping end portions 92 in the sliding block 41 of the respective one of the slide members 4. The structure and action of the locking means 5 are the same as those of the first embodiment. The structure and action of the single-direction positioning mechanisms 6 are the same as those of the first embodiment. Thereby, the fastening apparatus can be used to fasten two matrix bands 9 to two carious teeth at the same time.

While the present invention has been described in connection with what is considered the most practical and preferred embodiments, it is understood that this invention is not limited to the disclosed embodiments but is intended to cover various arrangements included within the spirit and scope of the broadest interpretations and equivalent arrangement.

I claim:

1. An apparatus for fastening two matrix bands to two teeth, each of said matrix bands having length-variable overlapping end portions and a loop portion extending from said overlapping end portions, said apparatus comprising:

an elongated support frame having front and rear ends and two opposite faces, said support frame having two retaining members which are formed spacedly adjacent to said front end of said support frame, each of said retaining members engaging slidably said overlapping end portions in order to orient selectively said loop portion of said matrix band to predetermined directions;

two elongated slide members, each of said slide members engaging slidably and parallelly with a respective one of said opposite faces of said support frame and having front and rear ends, said front end of each of said slide members being formed with a sliding block;

two locking means, each being provided on said sliding block of a respective one of said slide members for locking releasably a corresponding one of said overlapping end portions in said sliding block of said respective one of said slide members; and two single-direction positioning mechanisms, each permitting said sliding block of said respective one of said slide members to move away from a corresponding one of said retaining members of said support frame, but locking releasably said respective one of said slide members relative to said support frame in order to prevent said sliding block of said respective one of said slide members from being moved toward said corresponding one of said retaining members.

2. An apparatus for fastening a matrix band to a tooth, said matrix band having length-variable overlapping end portions and a loop portion extending from said overlapping end portions, said apparatus comprising:

an elongated support frame having front and rear ends, said front end of said support frame being formed with a retaining member that slidably engages said overlapping end portions in order to selectively orient said loop portion of said matrix band to predetermined directions;

an elongated slide member slidably engaging and in parallel with said support frame and having front and rear ends, said front end of said slide member being formed with a sliding block;

locking means provided on said sliding block of said slide member for releasably locking said overlapping end portions in said sliding block; and a single-direction positioning mechanism for permitting said sliding block of said slide member to move away from said retaining member of said support frame in order to pull said overlapping end portions of said matrix band to move rearwardly, thereby reducing the size of said loop portion of said matrix band, but releasably locking said slide member relative to said support frame in order to prevent said sliding block from being moved toward said retaining member, said single-direction position mechanism comprising a plurality of detent teeth that are formed adjacent said rear end of said slide member, and an elongated housing that is formed longitudinally adjacent said rear end of said support frame, said housing having a longitudinal hole for receiving said rear end of said slide member on which said detent teeth are formed, a transverse hole extending from an external face thereof to said longitudinal hole thereof, a lock pin received in said transverse hole, a coiled spring mounted in said transverse hole in order to bias said lock pin to move toward said external face of said housing, and a cam member connected pivotably to said housing within said transverse hole, said cam member being rotatable to a first position where said lock pin is pushed by said cam member against biasing force of said coiled spring so as to engage one of said detent teeth of said support frame, thereby permitting said sliding block to move away from said retaining member but preventing said sliding block from being moved toward said retaining member when said sliding block is moved away from said retaining member, and a second position wherein said lock pin is biased by said coiled spring so as to disengage said one of said detent teeth.

3. An apparatus for fastening a matrix band to a tooth, said matrix band having length-variable overlapping end portions and a loop portion extending from said overlapping end portions, said apparatus comprising:

an elongated support frame having front and rear ends, said front end of said support frame being formed with a retaining member that slidably engages said overlapping end portions in order to selectively orient said loop portion of said matrix band to predetermined directions;

an elongated slide member slidably engaging and in parallel with said support frame and having front and rear ends, said front end of said slide member being formed with a sliding block;

locking means provided on said sliding block of said slide member for releasably locking said overlapping end portions in said sliding block; and a single-direction positioning mechanism for permitting said sliding block of said slide member to move away from said retaining member of said support frame in order to pull said overlapping end portions of said matrix band to move rearwardly, thereby reducing the size of said loop portion of said matrix band, but releasably locking said slide member relative to said support frame in order to prevent said sliding block from being moved toward said retaining member, said single-direction positioning mechanism comprising an elongated housing formed adjacent said rear end of said support frame, said housing having a longitudinal through hole with a front end through which said rear end of said slide member extends and a rear end, a seal member that is mounted adjacent said front end of said longitudinal through hole and which contacts said slide member so that said slide member is slidably and sealingly extendible into said longitudinal through hole, and a check valve member mounted adjacent said rear end of said housing, thereby permitting air to flow from said longitudinal hole to an exterior of said housing but preventing air from flowing into said longitudinal through hole via said check valve member, whereby said sliding block can move away from said retaining member but is prevented from being moved toward said retaining member when said sliding block is moved away from said retaining member.

4. An apparatus for fastening a matrix band to a tooth, said matrix band having length-variable overlapping end portions and a loop portion extending from said overlapping end portions, said apparatus comprising:

an elongated support frame having front and rear ends, said front end of said support frame being formed with a retaining member that slidably engages said overlapping end portions in order to selectively orient said loop portion of said matrix band to predetermined directions;

an elongated slide member slidably engaging and in parallel with said support frame and having front and rear ends, said front end of said slide member being formed with a sliding block;

locking means provided on said sliding block of said slide member for releasably locking said overlapping end portions in said sliding block; and a single-direction positioning mechanism for permitting said sliding block of said slide member to move away from said retaining member of said support frame in order to pull said overlapping end portions of said matrix band to move rearwardly, thereby reducing the size of said loop portion of said matrix band, but releasably locking said slide member relative to said support frame in order to prevent said sliding block from being moved toward said retaining member, said single-direction position mechanism comprising a wedge-shaped groove formed transversely in an external face of said slide member adjacent said rear end of said slide member, a solid ball disposed in said wedge-shaped groove, and an elongated housing formed adjacent said rear end of said support frame, said housing having a longitudinal through hole with a front end through which said rear end of said slide member extends and a threaded rear end, two slits that extend from said threaded rear end and which are communicated with said longitudinal through hole in order to form a resilient tongue adjacent said rear end of said housing, and a screw member with a tapered, externally threaded shaft that threadably engages said threaded rear end of said longitudinal through hole, said ball being rolled and clamped between said slide member and an internal wall face of said longitudinal through hole in order to prevent said sliding block from being moved toward said retaining member, said ball being released when said screw member is threaded into said threaded rear end of said longitudinal through hole in order to permit free movement of said slide member relative to said support frame.

5. An apparatus for fastening a matrix band to a tooth, said matrix band having length-variable overlapping end portions and a loop portion extending from said overlapping end portions, said apparatus comprising:

an elongated support frame having front and rear ends, said front end of said support frame being formed with a retaining member that slidably engages said overlapping end portions in order to selectively orient said loop portion of said matrix band to predetermined directions;

an elongated slide member slidably engaging and in parallel with said support frame and having front and rear ends, said front end of said slide member being formed with a sliding block;

locking means provided on said sliding block of said slide member for releasably locking said overlapping end portions in said sliding block; and a single-direction positioning mechanism for permitting said sliding block of said slide member to move away from said retaining member of said support frame in order to pull said overlapping end portions of said matrix band to move rearwardly, thereby reducing the size of said loop portion of said matrix band, but releasably locking said slide member relative to said support frame in order to prevent said sliding block from being moved toward said retaining member, said locking means comprising a slit which is formed in a front end of said sliding block in order to receive said overlapping end portions of said matrix band, a transverse hole that extends from an external face thereof to said slit thereof, a lock pin received in said transverse hole, a coiled spring mounted in said transverse hole in order to bias said lock pin to move toward said external face of said sliding block, and a cam member pivotably connected to said sliding block within said transverse hole, said cam member being rotatable to a first position where said lock pin is pushed by said cam member against biasing force of said coiled spring so as to engage said overlapping end portions of said matrix band, thereby preventing separation of said overlapping end portions from said sliding block, and a second position where said lock pin is biased by said coiled spring so as to disengage said overlapping end portions of said matrix band.

6. A dual matrix band retainer comprising:

two matrix bands fastenable to two teeth, each of said matrix bands having length-variable overlapping end portions and a loop portion extending from said overlapping end portions;

an elongated support frame having front and rear ends and two opposite faces, said support frame having two retaining members that are formed spaced adjacent said front end of said support frame, each of said retaining members slidably engaging said overlapping end portions in order to selectively orient said loop portion of said matrix band to predetermined directions;

two elongated slide members, each of said slide members slidably engaging and in parallel with a respective one of said opposite faces of said support frame and having front and rear ends, said front end of each of said slide members being formed with a sliding block;

two locking means, each being provided on said sliding block of a respective one of said slide members for releasably locking a corresponding one of said overlapping end portions in said sliding block of said respective one of said slide members; and two single-direction positioning mechanisms, each permitting said sliding block of said respective one of said slide members to move away from a corresponding one of said retaining members of said support frame, but releasably locking said respective one of said slide members relative to said support frame in order to prevent said sliding block of said respective one of said slide members from being moved toward said corresponding one of said retaining members.

7. A dual matrix band retainer as claimed in claim 6, wherein said loop portions of said matrix bands are spot-welded to each other at a point that is to be disposed on a contact area of two adjacent teeth.

* * * * *

UNITED STATES PATENT AND TRADEMARK OFFICE
CERTIFICATE OF CORRECTION

PATENT NO. : 5,722,831
DATED : March 3, 1998
INVENTOR(S) : C.-S. Lin

It is certified that error appears in the above-identified patent and that said Letters Patent is hereby corrected as shown below:

COLUMN    LINE

10    32    "from end" should read --front end--
(Claim 6,  line 9)

Signed and Sealed this

Fourth Day of August, 1998

Attest:

BRUCE LEHMAN

Attesting Officer    Commissioner of Patents and Trademarks